US00PP30772P2

(12) United States Plant Patent
Hansen

(10) Patent No.: US PP30,772 P2
(45) Date of Patent: Jul. 30, 2019

(54) ***KNIPHOFIA* PLANT NAMED 'ROCKET'S RED GLARE'**

(50) Latin Name: *Kniphofia hybrida*
Varietal Denomination: Rocket's Red Glare

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,345

(22) Filed: Nov. 5, 2018

(51) Int. Cl.
*A01H 5/02* (2018.01)
*A01H 6/00* (2018.01)

(52) U.S. Cl.
USPC ..... Plt./443
CPC ..... *A01H 6/00* (2018.05); *A01H 5/02* (2013.01)

(58) Field of Classification Search
USPC ..... Plt./443
CPC ..... A01H 5/02
See application file for complete search history.

*Primary Examiner* — Kent L Bell

(57) ABSTRACT

A new and distinct cultivar of Red Hot Poker plant named *Kniphofia* 'Rocket's Red Glare' with long, mostly upright, strap-like, keeled, glaucous, gray-green foliage and numerous scapes beginning in late spring and continuing for up to fourteen weeks. The new plant resists lodging and the habit is densely growing, winter-hardy, tolerant of heat, deer and rabbits. Numerous scapes of vivid red flower buds on tall scapes maturing to pale yellow flowers. The new plant is useful for landscaping as a specimen, en masse, or as a long-lasting cut flower.

1 Drawing Sheet

Botanical classification: *Kniphofia hybrida.*
Variety denomination: 'Rocket's Red Glare'.

BACKGROUND AND ORIGIN OF THE PLANT

The present invention relates to the new and distinct Red Hot Poker, *Kniphofia* 'Rocket's Red Glare' hybridized under the direction of the inventor at a wholesale perennial nursery in Zeeland, Mich., USA on August 14 and seed harvested in the fall of 2012. The new plant was a single seedling selection resulting from a cross of 'Echo Rojo' U.S. Plant Pat. No. 22,791 as the female parent or seed parent and 'Papaya Popsicle' U.S. Plant Pat. No. 22,915 as the male parent or pollen parent. The plant passed initial evaluation in the summer of 2014 and was subsequently given the breeder code 12-5-9 prior to naming. *Kniphofia* 'Rocket's Red Glare' has been successfully asexually propagated by division method since 2014 at the same wholesale perennial nursery in Zeeland, Mich. and subsequently by shoot tip tissue culture, and both methods have been found to be stable and produce identical plants that maintain the unique characteristics of the original plant through multiple generations.

No plants of *Kniphofia* 'Rocket's Red Glare' have been sold, in this country or anywhere in the world, with this name or any other name, prior to the filing of this application, nor has any disclosure of the new plant been made prior to the filing of this application except that which was disclosed within one year of the filing of this application and was either derived directly or indirectly from the inventor.

SUMMARY OF THE PLANT

*Kniphofia* 'Rocket's Red Glare' differs from its parents as well as all other *Kniphofia* known to the applicant. The most similar known *Kniphofia* cultivars are: the female parent 'Echo Rojo', 'Redhot Popsicle' U.S. Plant Pat. No. 24,036, the male parent 'Papaya Popsicle', 'Fire Glow' U.S. Plant Pat. No. 22,894, 'Orange Vanilla Popsicle' U.S. Plant Pat. No. 24,292 and 'TNKNIPR' U.S. Plant Pat. No. 27,446. 'Echo Rojo' is slightly taller in scape height and buds are more orangish and not as deeply colored and the new plant has more flowers per scape. 'Redhot Popsicle' is much shorter in scape and foliage height with fewer flowers per scape that in bud are less intense and more orangish coloration. 'Papaya Popsicle' is significantly shorter in scape and foliage height with slightly more orangish flower bud color. 'Fire Glow' is much smaller in scape height, foliage height and overall habit and has a slightly more orangish flower bud color with less red hue. 'Orange Vanilla Popsicle' is much shorter in flower scape and foliage height and the flower bud color is a more reddish hue. 'TNKNIPR' is much shorter in scape height, similar in flower bud color, but the open flower color does not lighten as much as the new plant. 'Jackpot' U.S. Plant patent application Ser. No. 15/932,742 has slightly taller scapes with more orangish buds, longer season of bloom, and flowers that open to a brighter yellow.

*Kniphofia* 'Rocket's Red Glare' differs from these above cultivars and all cultivars known to the inventor in that it has:

1. Mostly upright, strap-like, keeled, gray-green foliage that resist lodging.
2. Moderately growing, dense habit, winter-hardy, heat tolerant, rabbit and deer tolerant, large-sized clumps.
3. Numerous scapes of vivid red flower buds lightening to pale yellow flowers on tall stems in maturity;
4. Flowering beginning the late spring and continuing for up to fourteen weeks in Michigan.

BRIEF DESCRIPTION OF THE DRAWINGS

The photographs of *Kniphofia* 'Rocket's Red Glare' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
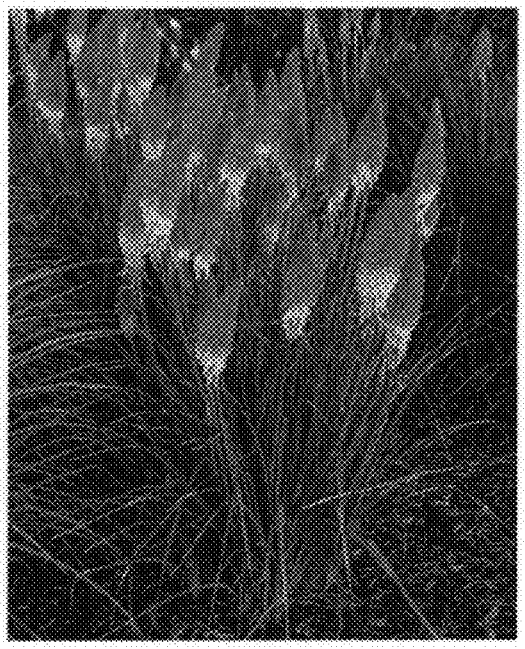
FIG. 1 shows the side-view habit of a five-year-old plant in midseason flowering.
Figure 2:
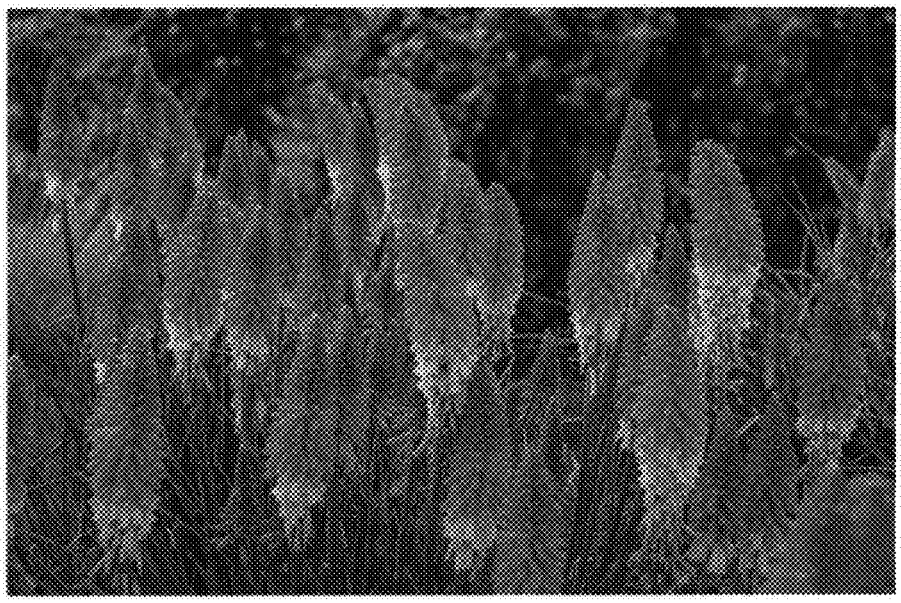
FIG. 2 shows a close-up of the flowers and buds.

The following descriptions and color references are based on the 2015 edition of The Royal Horticultural Society Colour Chart except where common dictionary terms are used. The new plant, *Kniphofia* 'Rocket's Red Glare', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Echo Rojo' as the female or seed parent and 'Papaya Popsicle' as the male or pollen parent;

Propagation method: By garden division of the crown and shoot tip tissue culture;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of crown, lightly branching; color nearest RHS 158C;

Plant description: Dense, rhizomatous, acaulescent, perennial clump with long thin foliage to about 100.0 cm across and about 75.0 cm tall; flowering to about 90.0 cm tall; about 62 peduncles per plant;

Leaves: Linear; keeled at base, triangular in distal half; arranged about 8 leaves per basal division; apex narrowly acute; base truncate, clasping; margin entire, micro-dentate to fibrillate; abaxial midrib micro-dentate; no fragrance observed;

Leaf size: To about 76.5 cm long and 15.0 mm across at base, average about 52.0 cm long and 13.0 mm across at base;

Leaf color: Young base nearest RHS 155B both abaxial and adaxial, distally nearest RHS 137C both abaxial and adaxial; mature adaxial nearest RHS 146B and abaxial nearest RHS 137C;

Leaf venation: Parallel; color same as leaf abaxial and adaxial;

Stem: Acaulescent; crown about 19.0 mm across at base;

Inflorescence: In spike-like raceme; terete; to about 185 flowers per stem, average about 160 flowers per stem; flowering portion to about 30.0 cm tall and about 6.0 cm across; lasting about three weeks; flower spacing less than 1.0 mm apart on raceme in distal region and about 2.5 cm in lowest flowers;

Peduncle: Cylindrical; solid not fistulose; glabrous; glaucous; erect to about 90.0 cm long and 8.0 mm diameter; average 85.0 cm tall and 7.5 mm diameter;

Peduncle color: Blend between RHS N144A and RHS 146D;

Buds one day prior to opening: Obellipsoidal with swollen subacute apex and rounded base; glabrous; slightly lustrous; about 18.0 mm long and about 3.0 mm diameter at base and 5.0 mm diameter at widest point near apex;

Bud attitude: Beginning outwardly and drooping as maturing toward anthesis;

Bud color: Abaxial distally nearest RHS 44A with veins nearest RHS 45A; proximally and underside base nearest 167B;

Flowers: Cylindrical forming tubular corolla; perfect; actinomorphic; individually open and effective about three to four days; about 21.0 mm long with exserted style and stamens and 6.0 mm across at face and 3.5 mm diameter near base;

Corolla size: To about 18.0 mm long, fused in basal about 17.0 mm; face to about 6.0 mm tall and about 6.0 mm wide; tube about 3.5 mm diameter near base and about 3.0 mm near fusion;

Flower attitude: Drooping;

Flower fragrance: None detected;

Flowering period: Individual racemes effective for about 3 weeks; beginning late spring in Michigan for about seven weeks;

Tepals: Six, in two sets of three; both sets identical with subacute apices and fused in basal 17.0 mm forming tube; margin entire; glabrous and lustrous abaxial and adaxial; about 18.0 mm long and about 3.0 mm across just above fusion point;

Tepal color (young abaxial): Nearest RHS 34A, with midrib nearest RHS 43A; (young adaxial): nearest RHS 37A with slight blushing midribs nearest RHS 39A;

Tepal color (mature abaxial): Nearest RHS 18C, with slight blushing of RHS 34B and dorsal veins RHS 34B; (mature adaxial): nearest RHS 18C with veins and slight blushing of nearest RHS N34B, midribs variable nearest RHS 160A and N167D;

Androecium: Six; variable lengths; exserted;

*Filaments*.—Six; exserted; cylindrical; glabrous; lustrous; variable lengths from about 16.0 to 21.0 mm long and about 0.5 mm diameter; color nearest RHS 2B.

*Anther*.—Ellipsoidal; dorsifixed; longitudinal; about 1.0 mm long and 0.7 mm diameter and 1.0 mm thick; color nearest RHS 17A.

*Pollen*.—Abundant: color nearest RHS 11A.

Gynoecium: Single; about 21.0 mm long;

*Style*.—Cylindrical; glabrous; lustrous; about 18.0 mm long and 0.7 mm diameter: color at anthesis nearest blend between RHS 168C and RHS 168D, at maturity nearest RHS 2C.

*Stigma*.—Flattened, round; puberulent; about 0.3 mm across; color nearest RHS 18D.

*Ovary*.—Superior; globose; rounded apex, truncate base; about 2.5 mm long and 2.0 mm diameter; color nearest RHS 146C.

Pedicel: Cylindrical; glabrous; stiff; drooping; about 1.5 mm long and about 1.0 mm diameter;

Pedicel color: Nearest RHS 173A;

Bracts: Ovoid; papery; translucent; at cauline nodes and subtending individual flowers; with acute apices and truncate base; to about 5.0 mm long and 2.5 mm across at middle; decreasing distally; average about 4.0 mm long and 2.0 mm across; color blushed with nearest RHS 161D;

Fruit: Tri-valved loculicidal capsule; ellipsoidal; about 7.5 mm long and 4.5 mm across; glabrous; with acute apex and rounded base; typically nine to twelve seeded; color upon maturity nearest RHS 200A;

Seed: Irregular with angular sides, acute apex and base; about 4.0 mm and 3.0 mm across; color nearest RHS 200A;

Disease and pest resistance: 'Rocket's Red Glare' is resistance to lodging but further resistance beyond that of other *Kniphofia* has not been observed. The plant grows best with good drainage and is able to tolerate some heat when established. Hardiness at least from USDA zone 6 through 9.

I claim:

1. A new and distinct variety of *Kniphofia* plant named 'Rocket's Red Glare' as herein described and illustrated.

* * * * *